United States Patent [19]
Myers et al.

[11] Patent Number: 5,851,553
[45] Date of Patent: Dec. 22, 1998

[54] PROCESS AND APPARATUS FOR MAKING RAPIDLY DISSOLVING DOSAGE UNITS AND PRODUCT THEREFROM

[75] Inventors: Garry L. Myers; Gerald E. Battist, both of Reston; Richard C. Fuisz, Great Falls, all of Va.

[73] Assignee: Fuisz Technologies, Ltd., Chantilly, Va.

[21] Appl. No.: 772,024

[22] Filed: Dec. 19, 1996

Related U.S. Application Data

[63] Continuation-in-part of Ser. No. 119,974, Sep. 10, 1993, Pat. No. 5,518,551, and a division of Ser. No. 652,252, May 23, 1996, Pat. No. 5,622,719, which is a continuation of Ser. No. 259,496, Jun. 14, 1994, abandoned, which is a continuation-in-part of Ser. No. 133,669, Oct. 7, 1993, Pat. No. 5,597,416.

[51] Int. Cl.$^6$ .............................. A61K 9/20; A61K 9/22
[52] U.S. Cl. ......................... 424/488; 424/464; 424/466; 514/960
[58] Field of Search .................................. 424/464, 466, 424/488, 439, 440, 441; 514/960

[56] References Cited

U.S. PATENT DOCUMENTS

| | | |
|---|---|---|
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,131,428 | 5/1964 | Mika . |
| 3,308,221 | 3/1967 | Opfell . |
| 3,324,061 | 6/1967 | Tanquary et al. . |
| 3,482,998 | 12/1969 | Carroll et al. . |
| 3,523,889 | 8/1970 | Eis . |
| 3,557,717 | 1/1971 | Chivers . |
| 3,595,675 | 7/1971 | Ash et al. . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0 287 488 A1 | 3/1988 | European Pat. Off. . |
| 0 387 950 A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2 155 934 | 3/1985 | United Kingdom . |
| WO 91/18613 | 5/1991 | WIPO . |

OTHER PUBLICATIONS

R.H. Doremus, "Crystallization of Sucrose From Aqueous Solution," *Journal of Colloid and Interface Science*, 104, pp. 114–120 (1985).

P. Bennema, "Surface Diffusion and the Growth of Sucrose Crystals," *Journal of Crystal Growth*, 3,4 pp. 331–334 (1968).

(List continued on next page.)

*Primary Examiner*—Robert H. Harrison
*Attorney, Agent, or Firm*—Sandra M. Nolan

[57] ABSTRACT

The present invention is a method of preparing rapidly dissolving comestible units such as tablets. The present invention also includes an apparatus for making the comestible units and the units themselves. The product prepared in accordance with the present invention can include active ingredients and is capable of dissolving in the mouth of the consumer within several seconds. The unit dosage forms prepared in accordance with the present invention are particularly useful as antacids and as a delivery vehicle for biologically active ingredients, especially those which are ideally combined with antacid ingredients in order to ameliorate the effects of antacid environment.

14 Claims, 2 Drawing Sheets

U.S. PATENT DOCUMENTS

| | | |
|---|---|---|
| 3,615,671 | 10/1971 | Schoaf . |
| 3,625,214 | 12/1971 | Higuchi . |
| 3,676,148 | 7/1972 | De Weese et al. . |
| 3,723,134 | 3/1973 | Chivers . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,992,265 | 11/1976 | Hansen . |
| 4,056,364 | 11/1977 | Dmitrovsky et al. . |
| 4,086,418 | 4/1978 | Turbak et al. . |
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,293,570 | 10/1981 | Vadasz . |
| 4,303,684 | 12/1981 | Pitchon et al. . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/1983 | Gregory et al. . |
| 4,376,743 | 3/1983 | Dees . |
| 4,492,685 | 1/1985 | Keith et al. . |
| 4,496,592 | 1/1985 | Kuwahara et al. . |
| 4,500,546 | 2/1985 | Turbak et al. . |
| 4,511,584 | 4/1985 | Percel et al. . |
| 4,526,525 | 7/1985 | Oiso et al. . |
| 4,585,797 | 4/1986 | Cioca . |
| 4,619,833 | 10/1986 | Anderson . |
| 4,772,477 | 9/1988 | Weiss et al. . |
| 4,793,782 | 12/1988 | Sullivan . |
| 4,855,326 | 8/1989 | Fuisz . |
| 4,872,821 | 10/1989 | Weiss . |
| 4,873,085 | 10/1989 | Fuisz . |
| 4,879,108 | 11/1989 | Yang et al. . |
| 4,885,281 | 12/1989 | Hanstein et al. . |
| 4,978,537 | 12/1990 | Song . |
| 4,997,856 | 3/1991 | Fuisz . |
| 5,011,532 | 4/1991 | Fuisz . |
| 5,028,632 | 7/1991 | Fuisz . |
| 5,034,421 | 7/1991 | Fuisz . |
| 5,073,387 | 12/1991 | Whistler . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,236,734 | 8/1993 | Fuisz . |
| 5,464,632 | 11/1995 | Cousin et al. ............................ 424/465 |

OTHER PUBLICATIONS

T.D. Simpson, et al., "Crystalline Forms of Lactose Produced in Acidic Alcoholic Media," *Journal of food Science,* 47 pp. 1948–1954 (1982).

A.D. Randolph, et al., "Continuous Sucrose Nucleation," *The International Sugar Journal,* pp. 8–12 (1974).

K.B. Domovs, et al., "Methanol–Soluble Complexes of Lactose and of other Carbohydrates," *J. Dairy Science,* 43, pp. 1216–1223 (1960).

A.D. Randolph, et al., "Continuous Sucrose Nucleation," *The International Sugar Journal,* pp. 35–38 (1974).

A.D. Randolph, et al., "Continuous Sucrose Nucleation," *The International Sugar Journal* pp. 73–77 (1974).

ICI Americas Inc., "ICI Americas Products for Cosmetics and Pharmaceuticals," (1977).

Domino Sugar Corporation, "Co–crystallization".

Domino Sugar Corporation, "Raspberry.".

Domino Sugar Corporation, "Molasses Dark".

PROCESS AND APPARATUS FOR MAKING RAPIDLY DISSOLVING DOSAGE UNITS AND PRODUCT THEREFROM

This application is a continuation-in-part of U.S. Ser. No. 08/119,974, filed Sep. 10, 1993, now U.S. Pat. No. 5,518, 551. It is also a division of U.S. Ser. No. 08/652,252, filed May 23, 1996, now U.S. Pat. No. 5,622,719, which was a continuation of U.S. Ser. No. 08/259,496, filed Jun. 14, 1994, now abandoned, which was a continuation-in-part of U.S. Ser. No. 08/133,669, filed Oct. 7, 1993, now U.S. Pat. No. 5,597,416. Reference is also made to U.S. application Ser. No. 08/259,258, filed Jun. 14, 1994 now abandoned, the disclosure of which is incorporated herein.

BACKGROUND OF THE INVENTION

The present invention relates to the art of making comestible dosage units, such as tablets, which dissolve rapidly in the mouth.

Dosage units in the form of tablets are usually prepared by compressing a formulation containing a medicinal substance or drug and other ingredients, such as excipients selected for properties which facilitate production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

The preparation of formulations for tabletting by wet granulation is the oldest method and still the most widely used. Wet granulation involves many steps, including: milling of drugs and excipients, mixing of the milled powders, preparation of binder solution, mixing of binder solution with powder mixture to form a wet mass, coarse screening of the wet mass using 6–12 mesh screens, drying of moist granules, screening of dry granules through 14–20 mesh screen, mixing of screen granules with lubricant and disintegrant, and tablet compression.

Wet granulation is an expensive process because it requires many processing steps and involves considerable material handling equipment. Consequently, the process requires both energy and substantial space which should be environmentally controlled.

Dry granulation refers to the granulation of a powder mixture by compression without the use of heat and solvent. Dry granulation is used when wet granulation is not available because the drug is sensitive to moisture or heat.

Two methods are used for dry granulation. One method is slugging, where the powder is precompressed on a heavy-duty tablet press, and the resulting tablets or slugs are milled to yield the granulation. The other method is precompression of the powder with pressure rolls using a compactor.

Dry granulation has many disadvantages. It requires a specialized heavy-duty tablet press to form the slug; it does not permit uniform color distribution as can be achieved with wet granulation, where dye can be incorporated into the binder liquid; the pressure roll press cannot be used with insoluble drugs because this may retard the dissolution rate; and the process tends to create dust thereby increasing the potential for cross-contamination.

Direct compression tabletting has the least amount of steps. Direct compression is used in a process by which tablets are compressed directly from powder blends of the active ingredient and suitable excipients (including fillers, disintegrants, and lubricants) which are included in the mix to provide uniform flow into the die cavity and form a firm solid compression tablet. No pretreatment of the powder blends by wet or dry granulation procedures is necessary.

Although it has considerably fewer steps than either wet or dry granulation processes, direct compression also has many technological limitations. These limitations include primarily obtaining sufficient flow, and obtaining bonding of particles to form a strong compressed tablet. Low-dose drugs are difficult to blend, that is, uniform distribution of the drug is not easily attained and unblending sometimes occurs during the compression stage. High-dose drugs do not lend themselves to direct compression because of poor flowability and poor compressibility. A typical example would be some of the antacid drugs, such as aluminum hydroxide and magnesium carbonate.

When direct compression is used the choice of excipients is extremely critical. It is desirable that when using direct compression fillers and binders possess both compressibility and fluidity. In addition to compressibility failures, the process of direct compression also has disadvantages in the area of blending. Direct compression blends are subject to unblending in post blending handling steps. Differences in particle size because of differences in density between drug and excipient particles may also lead to unblending in the hopper or feedframe on the tablet press.

A disadvantage of all prior art process is the production of fines usually associated with making compression tablets. In the prior art, preparation of particles for formulation of tablets by compression results in a noticeable amount of fines, i.e., very tiny particles on the order of 150 microns and less. These fines can interfere with operation of apparatus for feeding tabletting machines as well as the operation of the tabletting machines. Often, it is necessary to conduct tablet production in a facility which is environmentally controlled to eliminate or reduce the fines. This adds to the cost of production of the tablets.

Moreover, a percentage of the non-compressed particulate is lost during production because there are fines dispersed and cannot be recaptured, and because some of the fines are not capable of being recovered for recycle.

In order to overcome the disadvantages associated with the prior art set forth above, technology has been developed by the common owner of the present application and co-pending U.S. parent application Ser. No. 194,682 filed Feb. 10, 1994, now U.S. Pat. No. 5,654,003. The commonly-owned case discloses a unique procedure in which compression tabletting can be simply and accurately manufactured by "fuse and compression" steps. Fusion is achieved by flash flow processing the tablet ingredients to provide shearform matrix masses which are subsequently compressed to form comestible compression units. This process includes advantages of wet and dry granulation and direct compression but does not have the disadvantages associated with these prior art procedures.

Dr. Fuisz has several patents which relate to other unique delivery means. For example, in U.S. Pat. No. 4,855,326, Dr. Fuisz discloses a fiber form of medicament-bearing product which can be compacted to form a sheet-like body. He cautions, however, that the compact body cannot be squeezed too much for fear of breaking the fibrous mass. There is no indication to form a compressed tablet as a medicinal dosage form.

Similarly, in U.S. Pat. No. 4,873,085 a spun fibrous cosmetic is disclosed as well as a compacted form of sugar fibers to form a sheet-like body which can be handled more readily. There is no indication to form a compressed tablet.

In U.S. Pat. No. 4,997,856, a wafer-like structure is disclosed in which a medicament is distributed on or through spun fibers which are then chopped by passing through a conventional "food grinder" (Hobart hamburger grinder). The enclosed volume of the end product is less than 30%, and preferably less than 15%, of the as-spun volume of floss. There is no mention in the '856 disclosure to form a compressed tablet.

The use of compacted spun fibers in the same sense as in the patents mentioned above is also disclosed in U.S. Pat. No. 5,034,421 and U.S. Pat. No. 5,096,492. None of these disclosures suggest formation of a compressed tablet.

None of the procedures described above provide a technique for forming a rapidly dissolving dosage unit which can be manufactured, shipped and sold to consumers. It is, therefore, an object of the present invention to provide a method for preparing such a dosage unit.

Other and further objects will be realized by those skilled in the art in view of the following disclosure.

SUMMARY OF THE INVENTION

The present invention is a method of preparing a rapid or quick dissolve comestible unit by mixing uncured shearform matrix and an additive, molding the mixture to form a unit dosage form, and curing the shearform matrix. Preferably, the shearform matrix includes a crystallization enhancer and/or a binding aid.

The shearform matrix used to form dosage units in accordance with the invention can be made with flavors and/or sweeteners included in the feedstock used to make the matrix. Flavors can be chosen from natural and synthetic flavoring liquids. Sweeteners are those materials which provide sweetness to the matrix in addition to sweetness which is provided by the carrier material used to form the matrix, e.g., sucrose.

The mixture can be molded by being introduced in a unit dosage well and tamping the mixture therein. The tamped mixture is then cured by being subjected to environmental conditions of heat, moisture, and pressure which induce crystallization. For example, the unit can be cured by increasing the heat under substantially constant moisture condition. The heat can be increased by subjecting the tamped unit to microwave energy.

The additive, of course, is preferably an active ingredient such as a medicament.

Another type of additive which can be used in the present invention is an effervescent disintegration agent. The term effervescent disintegration agent(s) includes compounds which evolve gas. The preferred effervescent agents evolve gas by means of chemical reactions which take place upon exposure of the effervescent disintegration agent to saliva in the mouth. The agent or agents can be included in several ways in the units of the present invention. First of all the agents can be incorporated in the matrix by mixing with the feedstock prior to flash flow processing. Alternatively, the entire effervescent agent can be mixed with the shearform matrix after it has been produced by flash flow techniques. As yet a third alternative, one part of the agent can be included in the feedstock which is flash flow processed while the other part of the agent can be incorporated after flash flow processing. In any event, the effervescent disintegration agent provides for controlled and rapid disintegration of the tablet when placed in the mouth and provides for a positive organoleptic sensation by the effervescent action in the mouth. The texture, speed and sensation of disintegration can especially be adapted for use by children in combination with taking one or more of the medicaments contemplated for use in the present invention.

"Tamping" is used herein to mean that the mixture is subjected to compression pressure of less than about 500 lbs. per sq. in. (psi), preferably less than 250 psi, and most preferably from about 20 to about 100 psi.

Another method of identifying the compression force required to mold uncured matrix in accordance with the present invention is by identifying the density resulting from tamping. The product of the present invention should be compressed in its uncured condition to a density of not greater than about 1.2, preferably not greater than about 0.8, and most preferably not greater than about 0.65. In one most preferred embodiment, the density of the finished product is between 0.25 and 0.40.

The product prepared in accordance with the method set forth above can dissolve in the mouth of the consumer in less than 10 seconds. Usually, well made product produced in accordance with this process will dissolve within less than 5 seconds, and, most preferably less than 3 seconds. The most highly dissoluble units have been described as literally "exploding" in the mouth.

The present invention also includes a composition for delivering an active ingredient which includes the active ingredient incorporated in a molded saccharide-based crystalline structure. The composition also includes the saccharide-based structure which has a bi-dimensionally stabilized crystalline sugar. The sugar is produced by forming a sugar crystalline frame from an outer portion of an amorphous shearform sugar mass, and subsequently converting the remaining portion of the mass to a substantially completely crystalline structure. The product is preferably monodispersed and is also preferably microcrystalline. For definitions relating to monodispersed and microcrystalline as well as other definitions relating to the composition aspects of the present invention, reference is made to U.S. Pat. No. 5,597,416, which is incorporated herein by reference. The shearform mass can also include an additive which is co-crystallized in a crystalline product. The amorphous shearform mass is substantially rod-shaped, and has two dimensions lying in a cross-sectional plane of the rod. The single dimension extends along a linear axis of the rod. Preferably, the monodispersed structurally stabilized cross-section does not exceed 50 $\mu$m, and preferably does not exceed 10 $\mu$m.

Another embodiment of the present invention is an apparatus which implements the mixing and filling procedure, tamping, and curing in a continuous manufacturing process. The elements of the apparatus include a filler, tamper, and curing station. Preferred embodiments of the inventive apparatus include a mixer adjacent to, or in combination with, the filling station.

In another preferred embodiment, the apparatus also has a packaging capability. This can include a continuous feed package substrate and a forming station which provides the tamping wells which are subsequently filled with the mixed shearform product and additive. And, in yet a further preferred embodiment, the apparatus can include a sealer which seals the packaged end product followed by a station which separates the continuous packaging wells by, for example, a die punch. The entire apparatus can be followed in line by a carton filling station for preparing cartons and loads, such as palletized loads, for shipment.

Yet another manifestation of the present invention is a method of administering an active ingredient to a human host. The method includes ingesting a quick dissolve comestible unit prepared by the method of the present invention, i.e., mixing uncured shearform matrix and an active ingredient, followed by molding a unit dosage and curing the shearform matrix in the unit dosage form. The next step requires the host to retain the quick dissolve unit in the oral cavity for a time sufficient to contact the unit with water while in the oral cavity. Finally, the human host introduces water to the oral cavity while the unit is retained therein to enhance dissolution of the dosage unit.

As a result of the process and apparatus described herein, a rapidly dissolving dosage unit can be manufactured on a continuous basis and even prepared for shipment to the consumer in a single manufacturing line. The product can be made to provide the stunning sensation of exploding in the oral cavity upon ingestion by the consumer.

These and other advantages of the present invention will be appreciated from the detailed description and examples which are set forth herein. This description and the examples are set forth to enhance the understanding of the invention, but are not intended in any way to limit the scope thereof.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

The present invention includes a method of making quick dissolve comestible units, e.g., tablets. The units produced in accordance with the present invention have the capability of dissolving instantaneously in the mouth of the consumer. However, tablets can be produced, packaged, and distributed for sales without deteriorating during any process step along the way. In the past, tablets have been made primarily by compressing feedstock under high pressure in order to provide the necessary hardness for packaging and distribution. Consequently, prior art tablets so produced are limited in that they are not rapidly-dissoluble in the mouth. High density packing resulting from high compression tabletting hinders disintegration and wetting the interior portion of the tablet. This aspect of the prior art has been improved by the technology disclosed in parent U.S. application Ser. No. 194,682, filed on Feb. 10, 1994.

As a result of the present invention, however, a profound step forward has been made in the art of preparing dosage units which are intended to dissolve in the mouth. The tablets produced by the present invention dissolve within seconds. The product is prepared by a unique combination of processing steps. The invention also includes apparatus for making the tablets as well as the tablets (or dosage units) themselves.

The first step of the procedure is to mix an uncured shearform matrix and an additive, such as an active ingredient, to prepare for molding a unit dosage. "Shearform matrix" in the present invention means a matrix produced by subjecting a feedstock which contains a carrier material to flash flow processing.

Flash flow processing can be accomplished several ways. Flash-heat and flash-shear are two processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. The force necessary to separate and discharge flowable feedstock is centrifugal force which is produced by the spinning head.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material until the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992 entitled "Process For Making Shearform Matrix," which is incorporated herein by reference.

The feedstock for producing shearform matrix includes a carrier material. The carrier material can be selected from material which is capable of undergoing both physical and/or chemical changes associated with flash-flow processing. Materials useful as matrices may be chosen from those carbohydrates which are capable of forming free-form agglomerates upon being processed.

Preferred materials useful as matrices may be chosen from such classes as "sugars". "Sugars" are those substances which are based on simple crystalline mono- and di-saccharide structures, i.e., based on $C_5$ and $C_6$ sugar structures. "Sugars" include sucrose, fructose, lactose, maltose, and sugar alcohols such as sorbitol, mannitol, maltitol, etc. The preferred choice of sugar in the present invention is sucrose.

Preferred combinations of sugars includes sugars as used herein in combination with other mono-, di-, tri-, and polysaccharides up to 50% of the total amount, preferably up to 30% and most preferably up to 20%.

A shearform product is used in the technique of the present invention to obtain the new sugar product. A shearform sugar product is a substantially amorphous sugar which results from subjecting sugar to heat and shear sufficient to transform crystalline (usually granulated) sugar to amorphous sugar without the use of a solution. Thus, in the sense of the present invention, a shearform sugar product is characterized as a sugar product resulting from a non-solubilized sugar. It is the starting material for forming the unique crystalline product of the present invention.

Other carrier materials can be used, but preferably in combination with sugar—not as a total replacement.

Maltodextrins are an example of other carrier materials. Maltodextrins include those mixtures of carbohydrates resulting from hydrolysis of a saccharide feedstock which are described as solids having a DE of up to and including 65.

The feedstock can also include maltooligosaccharides produced by selective hydrolysis of cornstarch followed by removal of high and low molecular weight compounds. The general description of maltooligosaccharides as contemplated herein is set forth in co-pending U.S. application Ser. No. 07/847,595 filed Mar. 5, 1992, now U.S. Pat. No. 5,387,431.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of U.S. Pat. No. 5,279,849.

As previously mentioned, each of the carriers are used primarily in combination with sugars, and not as a total replacement.

Other materials which can be incorporated into the feedstock to enhance the shearform matrix include flavors and sweeteners (other than the carrier itself).

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., betacitral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Yet a further embodiment of the present invention includes the use of an effervescent disintegration agent. Its action can aid in the masking of objectionable taste of active ingredients such as vitamins, medicines and/or minerals, etc. It is generally believed that the positive organoleptic sensation achieved by the effervescent action in the mouth, the texture, speed and sensation of disintegration aids in masking undesirable flavor notes in the mouth.

In preferred embodiments of the present invention, the effervescent disintegration agent may include at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

Inasmuch as the term effervescent refers to those agents which evolve gas, the bubble or gas generating the action is most often the result of the reaction of a soluble acid source and an alkali metal carbonate or carbonate source. The reaction of these two general classes of compounds produces carbon dioxide gas upon contact with water included in saliva. Carbonate sources include dry solid carbonate and bicarbonate salts such as sodium bicarbonate, sodium carbonate, potassium bicarbonate and potassium carbonate, magnesium carbonate and sodium sesequicarbonate, sodium glycine carbonate, L-lysine carbonate, arginine carbonate and amorphous calcium carbonate. While the food acids can be those indicated above, acid anhydrides of the above-described acids may also be used. Acid salts may include sodium, dihydrogen phosphate, disodium dihydrogen pyrophosphate, acid citrate salts and sodium acid sulfite. Other source of effervescence can be included and the present invention is not limited to those specifically set forth herein.

Also as previously mentioned, the ingredients of the effervescent agent can be included in one of at least three different ways. The first method includes incorporating the entire effervescent agent in the feedstock which is used to form the shearform product. The second manner of incorporating an effervescent disintegrating agent is to include the entire agent as an additive which is mixed with shearform matrix after it is formed. The third method contemplates incorporating one portion of the disintegrating agent in the shearform matrix and another portion of the disintegrating agent as an additive after formation of the shearform matrix material. The artisan will determine the best way to preserve the agent for its disintegrative and effervescent properties upon ingestion by the host.

The shearform matrix used in the inventive process must be uncured before it is molded. "Uncured" means amorphous or having a degree of amorphousness which enables the formation of a dosage unit upon curing. "Curing" means transforming the matrix from amorphous to crystalline while being sufficiently bound to produce a stable structure.

Curing can be enhanced by crystallization modifiers. Crystallization modifiers can be added to the feedstock before flash flow processing, such modifiers include, but are not limited to, surfactants (Spans™ and Tweens™), dextrose, polyethylene glycol (PEG), polypropylene glycol (PPG), etc. These modifiers generally provide controlled acceleration of crystallization while the matrix is bound.

Crystallization modifiers enhance the formation of a crystalline frame and the conversion of the remaining mass. Enhancement as used with respect to the process of the present invention principally means acceleration of the process. Enhancement also includes contribution to the strength of the crystalline structure, and predictability of results. Other benefits such as reduced-size product also is achieved by use of crystallization modifiers.

Crystallization modifiers, which are preferably added to sugars before being processed to amorphous shearform mass (or can be coated on the sugar), are used to affect the rate of crystallization. Water itself is a crystallization modifier, and is preferably included in the amorphous shearform sugar mass in an amount of between about 0.5% to about 2.0%. Non-saccharide hydrophilic organic materials (NSHMs) are also used as crystallization modifiers. Even though some NSHMs are surfactants, other materials can be used. Materials found to be most effective have a hydrophilic to lipid balance (HLB) of 6 or greater, i.e., they have the same degree of hydrophilicity as surfactants characterized by degree of HLB. Such materials include, but are not limited to anionic, cationic, zwitterionic surfactants as well as neutral materials which have an HLB of six (6) or greater. Preferred NSHMs are hydrophilic materials having polyethylene oxide linkages. Also, the preferred NSHM's have a molecular weight of at least 200 and preferably at least 400.

Lecithin is one surface active agent for use in the present invention. Lecithin can be included in the feedstock in an amount of from about 0.25 to about 2.00% by weight. Other surface active agents include, but are not limited to, the Spans™ and Tweens™ which are commercially available from ICI Americas Inc. Carbowax™ is yet another crystallization modifier which is very useful in the present invention. Preferably, Tweens™ or combinations of surface active agents are used to achieve the desired HLB.

By use of a surfactant the process and product of the present invention can be reproduced with a high degree of predictability. As additional crystallization modifiers which enhance the procedure and product of the present invention are identified, Applicants intend to include all such additional crystallization modifiers within the scope of the invention claimed herein.

The process of the present invention requires mixing an additive with the uncured shearform matrix. When the shearform matrix is in the form of a floss, it is preferably chopped first to reduce the volume of the product without compressing it. The additive can be any ingredient or ingredients needed to supply the dosage unit with the required characteristics. The primary ingredients are medicinal substances.

Medicinal substances which can be used in the present invention are varied. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Especially preferred active ingredients contemplated for use in the present invention are antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include aspirin, acetaminophen, and acetaminophen plus caffeine.

Other preferred drugs for other preferred active ingredients for use in the present invention include antadiarrheals such as immodium AD, antihistamines, antitussives, decongestants, vitamins, and breath fresheners. Also contemplated for use herein are anxiolytics such as Xanax; antipsychotics such as clozaril and Haldol; non-steroidal anti-inflammatories (NSAID's) such as Voltaren and Lodine; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigraines such as Imigran, ACE-inhibitors such as Vasotec, Capoten and Zestril; Anti-Alzheimers agents, such as Nicergoline; and $Ca^H$-Antagonists such as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Other ingredients which may be included are fragrances, dyes, sweeteners both artificial and natural, and other additives.

For example, fillers may be used to increase the bulk of the tablet. Some of the commonly used fillers are calcium sulfate, both di- and tri basic, starch, calcium carbonate, microcrystalline cellulose, modified starches, lactose, sucrose, mannitol, and sorbitol.

Other ingredients includes binders which contributes to the ease of formation and general quality of the tablet. Binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Lubricants can also be used to aid in tamping and compacting. Lubricants can include, but are not limited to, the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, disintegrants can be used to enhance the dispersibility of the compressed tablet in an aqueous environment. The dispersants can include starch, alginic acid, guar gum, kaolin, bentonite, purified wood cellulose, sodium starch glycolate, isoamorphous silicate, and microcrystalline cellulose. In view of the highly dissoluble nature of the product of the present invention, there is little need for disintegrants.

Another ingredient useful in tabletting are glidants which adhere to the cohesive material in order to enhance flow properties by reducing interparticle friction. Glidants which can be used include starch, talc, magnesium and calcium stearate, zinc stearate, dibasic calcium phosphate, magnesium carbonate, magnesium oxide, calcium silicate, and silica aerogels.

Color additives useful in preparing tablets include food, drug and cosmetics (FD&C) colors, drug and cosmetic (D&C) colors, or external drug and cosmetic (Ext. D&C) colors. These colors are dyes, their corresponding lakes, and certain natural and derived colorants. Lakes are dyes absorbed on aluminum hydroxide.

In a preferred embodiment, the present invention is particularly useful in preparing antacid tablets. Antacids are conveniently provided in chewable tablet form to provide a convenient method of delivering antacid to the consumer. The chewable form provides an advantage in that the tablet is broken up into granules during chewing and mixed with saliva before swallowing. This renders the tablet antacid formulation a suspension. One of the disadvantages of prior art antacid tablets is that the mass of ingredients residing in the mouth during and after chewing have objectional texture and taste. The present invention overcomes these disadvantages because the ingredients virtually explode into dissolution. The texture is also significantly enhanced and the residence time is substantially reduced.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

After the ingredients of the "additive" have been mixed with the uncured shearform matrix, the result of mixture must be "molded" as a unit dosage form.

"Molding" is used herein to mean associating uncured (i.e., uncrystallized) shearform matrix material closely enough to provide bridging between crystallized matrix material upon curing. Generally, this requires force sufficient to provide intimate contact of fibers prior to curing, followed by crystallizing to form a bound continuous crystalline structure throughout the tablet. Unlike conventional tabletting which relies primarily on compression to provide the structure, the present process utilizes the curing process to aid in forming the end product. Consequently, mild compression forces can be used to mold the product. In a preferred embodiment, the compression required to mold uncured matrix material is referred to as "tamping."

"Tamping" means compressing with force less than that required in compression tabletting, which is generally regarding as being on the order of thousands of pounds per square inch (psi). The maximum pressure used in the present invention is only 500 psi, but in most cases will never exceed about 250 psi, and, in the most preferred embodiments, not more than 80 psi (e.g., 40 psi to 80 psi). These lower pressures are called tamping.

Another method of measuring the compression force required to "mold" uncured matrix is by product density. The product of the present invention should be compressed in an uncured condition to a density of not greater than about 1.20, preferably not greater than 0.8, and, most preferably, not greater than 0.65.

Inasmuch as the present invention requires extremely low pressures for molding, it is possible to mold directly in plastic product wells which can be used as packaging for sales. Consequently, the present invention includes the concept of molding uncured matrix materials clearly in product wells such as plastic blister package depressions.

After preparing shearform matrix and molding the uncured matrix, the product must be cured. Curing means binding and crystallizing the matrix material substantially simultaneously. Curing is performed by subjecting product to heat and moisture sufficient to provide controlled crystallization. Controlled crystallization occurs when points of contact of uncured matrix material become points of crystalline growth and crystallization of the material proceeds to provide crystalline structures. Binding occurs at the points of contact, and the simultaneous crystalline growth is such as to maintain structural integrity.

The "curing" process of the present invention involves a transformation from amorphous to crystalline state. The transformation must take place while the amorphous shearform matrix remains bound together.

Moreover, curing requires the transformation to take place without collapsing the structural integrity of the matrix in its "formed" condition. Since amorphous shearform product is hygroscopic, this transformation can be difficult. When points of contact between pieces of matrix can be made points of crystalline growth during curing, structural integrity is established and maintained. One way of promoting the occurrence of this phenomenon is to include crystallization enhancers, e.g., surfactants, any alcohol, polyethylene glycol, polypropylene glycol, etc. Without being bound by theory, it is believed control of the propagation of crystalline growth as outlined above is improved significantly by use of crystallization enhancers.

Prior to curing, the mixture of shearform matrix and active are maintained at temperature and humidity below the glass transition temperature of the shearform matrix material.

Conditions suitable for curing can include ambient conditions of heat and moisture or modified ambient conditions. For example, it has been found that curing can be conducted at a temperature of 0°–90° C. at a relative humidity of 25–90%. In one case, it has been found that curing will take place within 15 minutes at 40° C. and 85% r.h. In other cases, optimum temperature range has ben found to be at 20°–50° C. Microwave energy can be used to controlledly accelerate curing.

Generally, the crystallization is effected in an environment wherein the tabletted material cures to a water content of less than 5% by weight, and preferably less than 1% by weight based on the weight of the tablet. Thus, the curing environment, e.g., chamber or room, is maintained at a relative humidity which permits water pickup no greater than 5%, and preferably less than 1%.

It has been found that curing product in a package well results in shrinkage of the tablet from the walls of the well. This feature is particularly advantageous for purposes of manufacturing individual dosage units since molding and curing can be performed in the package used for commercial sales. Consequently, several transfer steps can be eliminated.

Products prepared in accordance with the present invention have been found to have densities of from about 0.20 gm/cc$^2$ to about 0.90 gm/cc$^2$, and some preferred embodiments have densities of from about 0.40 gm/cc$^2$ to about 0.65 gm/cc$^2$.

Another ingredient which can be included in the shearform matrix is a binding aid or agent. A binding agent is used to assist in the molding step and, in some is cases, contributes to the dissolution capabilities of the finished product. Binding agents useful herein include low-glass-transition materials. Some agents found useful include, but are not limited to, sorbitol, mannitol, lactose, etc. The binding agents are flash flow processed with the carrier. Binding agents also aid in holding the matrix material in place for curing. In some cases portions of the binder becomes part of the matrix material.

Figure 1:
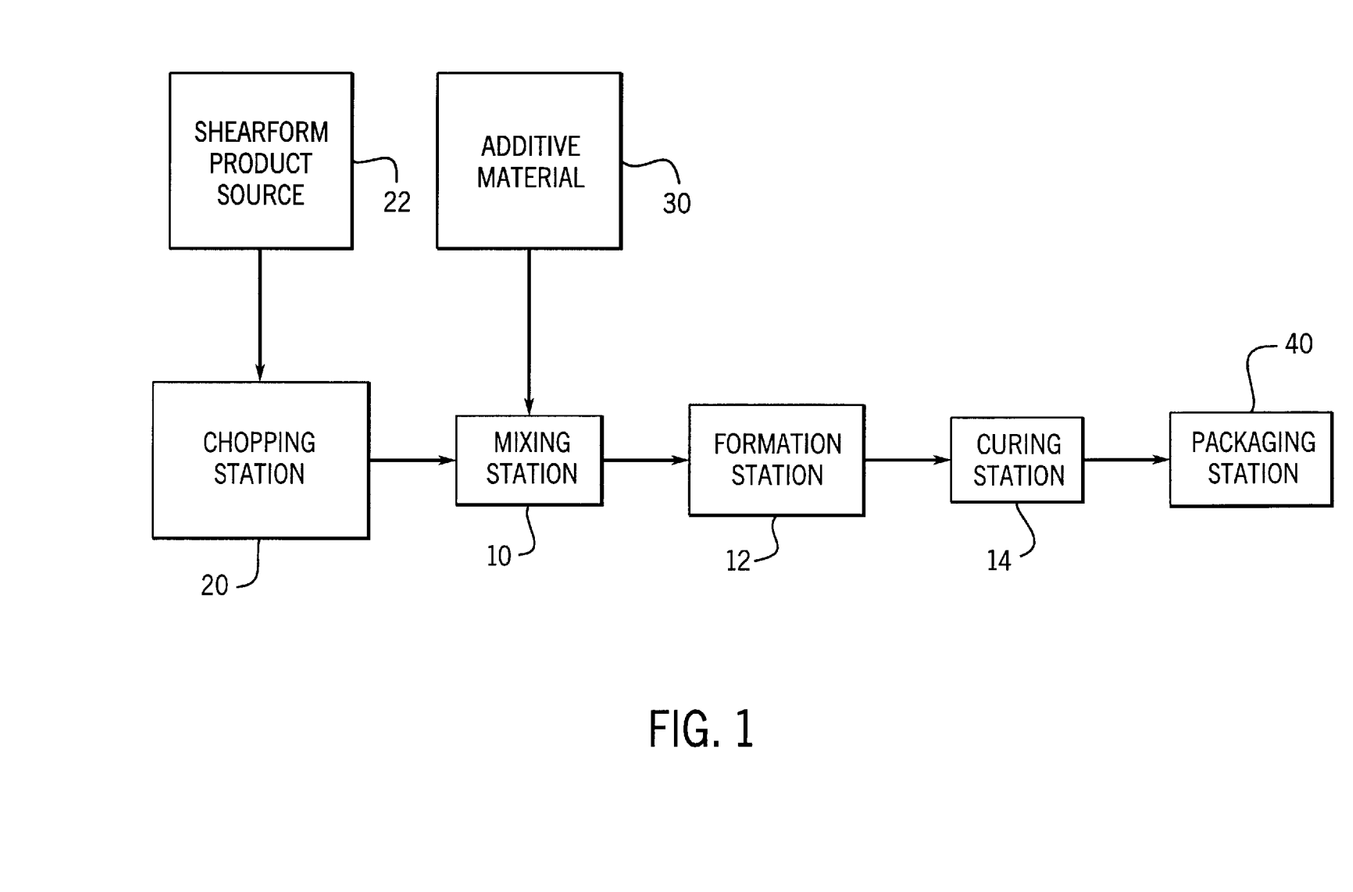
FIG. 1 is a block diagram of the process and apparatus of the present invention.

Referring to FIG. 1, a schematic of the process and apparatus in accordance with the present invention is shown. In particular, a mixing station 10 is shown in combination with a formation station 12 and a curing station 14, which are located in series and downstream of the mixing station 10. The mixing station 10 can receive feedstock from a source of shearform product 22. The source of shearform product can be flash flow process apparatus such as those been previously described herein. The source of shearform product can also include weighing apparatus. Premixing apparatus can also include a macerating (or chopping) station 22, in which shearform product in the form of floss can be chopped.

The mixing station 10 can also receive additive material from a station 30. The station 30 can also include weighing and mixing apparatus so that the additive can be properly prepared before it is mixed with the shearform product in station 10.

In forming station 12, dosage units are formed by tamping. The dosage units formed in station 12 are then transferred to curing station 14 which can include heat, pressure and moisture control means for providing the type of curing desired.

Optionally, the process of the present invention can also include a packaging station 40.

Figure 2:
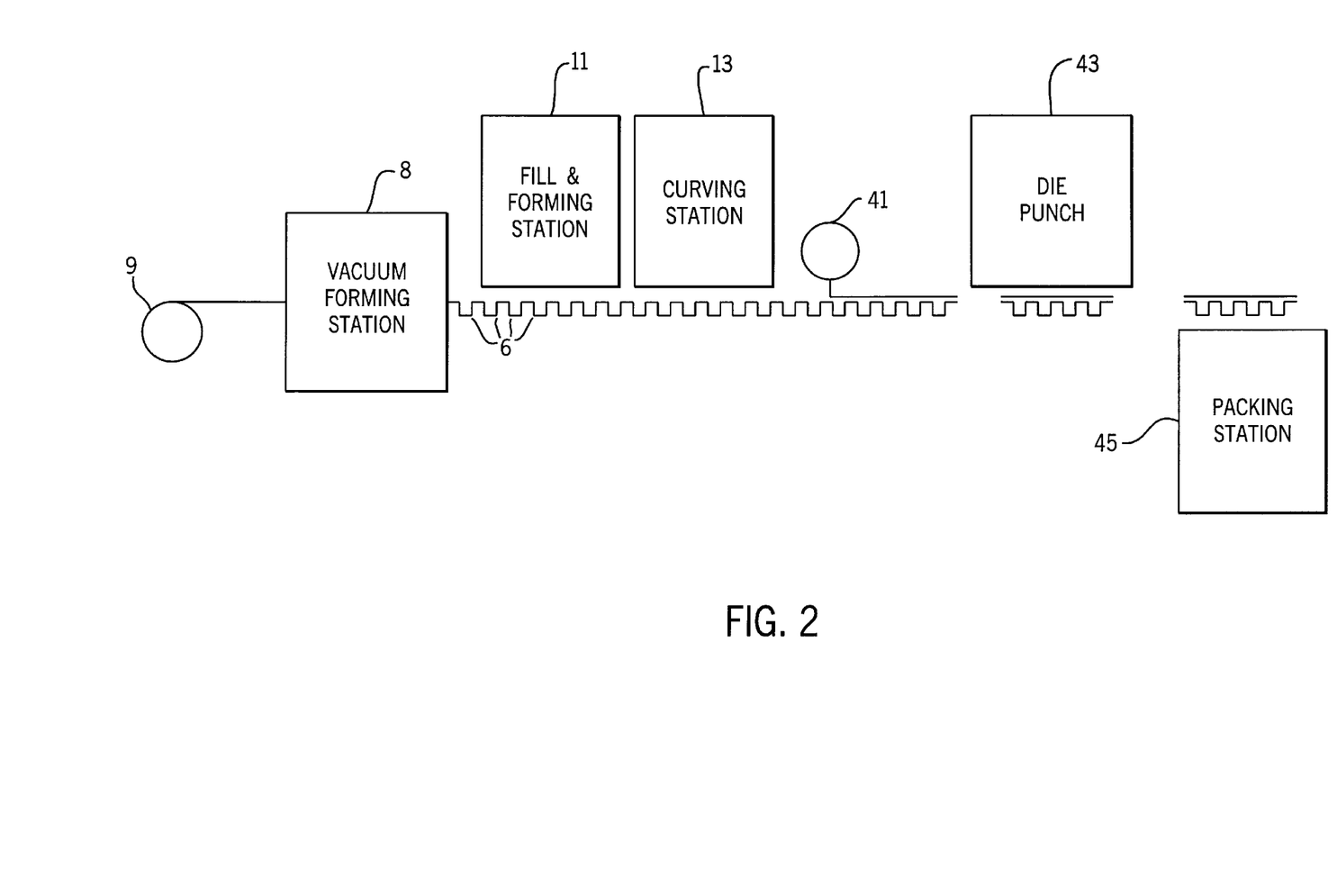
FIG. 2 is a schematic of a preferred embodiment of a process and apparatus in accordance with the present invention.

In order to demonstrate a preferred form of the invention, reference is made to FIG. 2. In FIG. 2, an in-line apparatus and schematic process is depicted wherein plastic stock material can be continuously provided from stock roll 9. Plastic stock can then be formed into a continuous tray having product wells 6 by vacuum forming at vacuum forming station 8. Each of the wells 6 can be filled at fill and forming station 11.

Fill and forming station 11 in FIG. 2 includes stations 10 and 12 of the schematic process shown in FIG. 1. That is to say, both the shearform product and an additive can be mixed, delivered to each of the wells 6, and formed by tamping at station 11 shown in FIG. 2. Proceeding along the process of FIG. 2, the product can then be cured at curing station 13.

Lid stock, such as continuous sheet material can be fed from a stock roll 41, and joined in a secure fashion (such as by adhesion) to the top of the continuous plastic tray material 9 thereby sealing product wells 6.

In order to obtain unit packaging suitable for sales to individual customers, the continuous sheet can then be separated into customer size lengths by a die punch 43. Finally, the customer size packages can then be boxed in a carton at a packing station 45. The cartons can then be loaded for shipment as, for example, in a palletized configuration.

The present invention has been found to be ideally suited for preparation of antacid tablets and tablets in which antacids are used as an ingredient to ameliorate the acid conditions in the body in order to assist drugs which do not tolerate acidic conditions. In the case of antacids themselves, the instantaneous dispersion of the tablet in the mouth prevents the residual chalky taste of a conventional antacid tablet. In the case of ingredients which do not tolerate acidic conditions, it is desirable to include the antacids plus the "acid-sensitive" pharmaceutical in a dosage unit prepared according to the invention. For example, didanosine is an antiviral agent which does not tolerate an acidic environment well. Consequently, the use of didanosine in combination with an antacid such as calcium carbonate in the same drug delivery system is an ideal method of introducing the drug to the body. The present invention includes the combination of an "acid-sensitive" ingredient and an antacid in a dosage unit.

Actual tests have been conduced to show the efficacy of the present invention. These examples have been set forth herein for the purpose of illustration and demonstration. The scope of the invention, however, is not to be in any way limited by the examples.

The shearform matrix material used in the following examples is an amorphous sugar. Amorphous sugar as used herein means a sugar stock which contains a high percentage of amorphism, i.e., greater than 50% by weight, and preferably greater than 70% by weight of the sugar stock is amorphous.

In all examples the shearform matrix was analyzed by both Differential Scanning Calorimetry (DSC) and polarized light under a microscope. In each case the shearform matrix was formed to be substantially amorphous before the active ingredient was added.

EXAMPLES

Antacid Example

A shearform matrix was prepared for use in the process of the present invention. The matrix was prepared by subjecting a blend of appropriate ingredients and subjecting to flash flow processing in a cotton candy type apparatus. The combination included the saccharide-based carrier material sucrose, sorbitol as a binding agent, and a surfactant known as Tween™ 60 provided by ICI. The blend was provided according to the formula set forth below in the Shearform Matrix Table 1.

TABLE 1

| SHEARFORM MATRIX | | |
|---|---|---|
| Ingredient | Amount By Weight | Percentage |
| Sugar (Sucrose) | 64.75 g | 84.75% |
| Binding Agent (Sorbitol) | 15.00 g | 15.00% |
| Surfactant (Tween ™ 60) | 0.25 g | 0.25% |
| Totals | 100.00 g | 100.00% |

The sorbitol, sucrose and surfactant were mixed by hand, then mechanically in a mixing apparatus. The resulting mixture was introduced to an Econo Floss™ machine and flash flow processed at approximately 3,600. The shearform matrix resulting from the processing was an uncured white floss which was reduced in volume by chopping.

After preparation of the shearform matrix, an additive was mixed with uncured matrix material. The total combination is set forth below in the Unit Dosage Table 2.

TABLE 2

UNIT DOSAGE

| Ingredient | Percentage |
| --- | --- |
| Shearform Matrix (Floss From Table 2) | 46.70% |
| Calcium Carbonate (CaCO$_3$) | 50.00% |
| High Intensity Sweetener (Aspartame ™) | 0.30% |
| Flavoring | 2.50% |
| Polyethylene Glycol (PE9 300) | 0.50% |
| | 100.00% |

The ingredients set forth above were mixed in order to prepare for forming and curing. The mixture resulting from Unit Dosage Table 2 was weighed out in 0.75 g samples and introduced to molds approximately 0.75 inches in diameter. Tablets were formed by tamping the ingredients at pressures of both 60 psi and 80 psi. The formed tablets were cured in an oven at 40° C. and 85% relative humidity for approximately 15 minutes.

The resulting tablets were very attractive looking having a smooth and shiny surface. The tablets were also prepared in a smaller mold having a diameter of about 0.65 inches. Similarly, the smaller tablets were molded at 60 psi and 80 psi and cured in accordance with the procedure set forth above. The resulting product also had an attractive appearance with a smooth and shiny surface.

The tablets resulting from this procedure were very fast melt. They did not have a chalky mouthfeel during consumption. The taste was excellent.

Antacid Example 2

The procedures set forth above was repeated with a different antacid formulation. The new formulation also used the chopped or macerated floss prepared in accordance with Shearform Matrix Table 1. The new formulation is set forth in Unit Dosage Table 3.

TABLE 3

UNIT DOSAGE

| Ingredient | Percentage |
| --- | --- |
| Shearform Matrix (Floss From Table 1) | 46.20% |
| Calcium Carbonate (CaCO$_3$) | 50.00% |
| High Intensity Artificial Sweetener (Aspartame ™) | 0.30% |
| Flavoring | 2.50% |
| Polyethylene Glycol (PEG 300) | 0.50% |
| Dye (Red FD&C No. 40) | 0.50% |
| | 100.00% |

Tablets were made similarly to the process set forth with regard to Unit Dosage Formula 2, both with large and smaller molds and at both 60 psi and 80 psi. The color tablets produced in accordance with the third unit dosage formula were similar to those produced with the first formula. The tablets made with the third formula were very quick dissolving and they had a smooth and shiny surface. After four days, the tablets had set. They did not manifest a chalky mouthfeel when consumed. The tablets retained structural stability while in the product wells.

Tablets prepared in accordance with Formula 2 and Formula 3 had sufficient hardness for subsequent handling and distribution to consumers.

Ibuprofen Example

A shearform matrix material was prepared in accordance with the formula set forth in Shearform Matrix Table 4.

TABLE 4

SHEARFORM MATRIX

| Ingredient | Percentage |
| --- | --- |
| Sugar (Sucrose) | 84.75% |
| Binding Agent (Sorbitol) | 12.00% |
| Binding Agent (α Lactose) | 3.00% |
| Surfactant (Tween ™ 80) | 0.25% |
| Total | 100.00% |

The sucrose, sorbitol and lactose were mixed first by hand and then by machine until a homogenous blend was produced. To this mixture, the surfactant was added and mixed by hand. The blend was then subjected to flash flow processing in a Econo Floss Machine No. 7025 at approximately 3,600 rpm at a temperature setting of high. The spun material was collected as a floss and macerated in a mixing machine for about 45 seconds. The resulting material was a reduced volume shearform matrix in uncured condition.

An ibuprofen mixture was prepared in accordance with the present invention in accordance with the formula set forth below in Ibuprofen Table 5.

TABLE 5

IBUPROFEN

| Ingredient | Amount By Weight | Percentage |
| --- | --- | --- |
| Shearform Matrix (Floss From Table 4) | 54.41 g | 60.46% |
| Ibuprofen (Microcaps) | 28.88 g | 32.09% |
| Flavor | 5.40 g | 6.00% |
| High Intensity Artificial Sweetener (Aspartame ™) | 0.72 g | 0.80% |
| Lecithin (Yelkin DS) | 0.32 g | 0.35% |
| Silica (Syloid 244) | 0.23 g | 0.25% |
| Orange Color | 0.05 g | 0.05% |
| Totals | 90.01 g | 100.00% |

The lecithin and ibuprofen was mixed and added to the ground floss material. The ingredients were mixed in a mechanical mixing apparatus for 15–20 seconds. The flavors, high intensity sweetener, syloid were then added and mechanically mixed with an additional 10–15 seconds. Finally, the color was added and mixed until the blend took on a homogenous orange color.

The ingredients mixed well on a large scale. The mixture had a homogenous density and excellent flow characteristics. The mixture was added in portions of 0.75 grams to a die having a 0.65 inch diameter. The ingredients were then tamped at a pressure of 80 psi.

The tamped dosage units were then cured. Some of the tablets were cured for one day at room temperature and then the packages were sealed for testing at a later date.

In general, the tablets resulting after curing were smooth and easy to handle without disintegration of the tablet units. Moreover, the tablets dispersed quickly in the mouth and produced little or no unwanted mouth feel.

The ibuprofen product included highly desirable unit dosages suitable for consumer ingestion.

Aspirin Example

A shearform matrix was prepared in accordance with the same formula and procedure as set forth above with respect to the ibuprofen example. An aspirin sample formulation was prepared in accordance with the amounts set forth below in Aspirin Table 6.

TABLE 6

ASPIRIN

| Ingredient | Amount By weight | Percentage |
|---|---|---|
| Shearform Matrix (Floss From Table 4) | 17.10 g | 62.18% |
| Aspirin | 9.00 g | 32.73% |
| Flavor | 1.00 g | 3.64% |
| High intensity Artificial Sweetener (Aspartame ™) | 0.25 g | 0.91% |
| Wetting Agent-Lecithin (Yelkin DS) | 0.10 g | 0.36% |
| Flow Agent | 0.05 g | 0.18% |
| (Syloid 244 FP) | | |
| Totals | 27.50 g | 100.00% |

The aspirin and lecithin were mixed and then added to the chopped shearform matrix. These ingredients were mixed and then the flavors and high intensity sweeteners were added and mixing was continued. Finally, the flow agent and colors were added and mixing continued until a homogenous mixture was obtained.

The blend was introduced to product wells and then tamped at 80 psi to form aspirin containing dosage units. The tablets were then cured by permitting them to remain at room temperature for approximately one day. These samples were tasted and it was found that the dosage units dissolved in the mouth in less than 5 seconds. The flavor was good and there was no chalky residue or mouthfeel in the oral cavity.

Another aspirin example was prepared in accordance with the table set forth below.

TABLE 7

ASPIRIN

| Ingredient | Amount By Weight | Percentage |
|---|---|---|
| Shearform Matrix (Floss From Table 4) | 14.60 g | 58.40% |
| Aspirin | 9.00 g | 36.00% |
| High Intensity Artificial Sweetener (Aspartame ™) | 0.25 g | 1.00% |
| Flavor | 1.00 g | 4.00% |
| Wetting Agent-Lecithin (Yelkin DS) | 0.10 g | 0.40% |
| Flow Agent | 0.05 g | 0.20% |
| (Syloid 244 FP) | | |
| Totals | 25.00 g | 100.00% |

Twenty tablets were prepared in accordance with the procedure set forth above with the respect to the first aspirin examples. That is to say, unit dosages were tamped at 80 psi and permitted to cure overnight at room temperature and humidity. The resulting tablets were attractive and had a good taste and texture. They melted quite rapidly in the mouth, i.e., generally in less than 5 seconds.

Acetaminophen Example

The floss used in the acetaminophen preparations is the same floss that was prepared in accordance with the Shearform Matrix Table 4. A blend of ingredients was prepared in accordance with the formula set forth below in Acetaminophen Table 8.

TABLE 8

ACETAMINOPHEN

| Ingredient | Amount By Weight | Percentage |
|---|---|---|
| Shearform Matrix (Floss From Table 4) | 11.01 g | 44.04% |
| Acetaminophen | 12.19 g | 48.76% |
| Flavor | 1.50 g | 6.00% |
| High Intensity Artificial Sweetener (Aspartame ™) | 0.20 g | 0.80% |
| Wetting Agent-Lecithin (Yelkin DS) | 0.09 g | 0.35% |
| Totals | 24.99 g | 100.00% |

The spun and chopped shearform matrix was mixed with the acetaminophen and lecithin to coat the drug. Additional chopped shearform matrix was mixed until a homogenous mixture result. The remaining ingredients were added and blended until a uniform mixture was obtained.

Samples of 0.90 grams of the tablet mix were introduced into tablet molds. The tablets were formed by tamping with 60 psi.

Half of the tablets were cured at 40° C. and 80% relative humidity for 15 minutes in order to cure. The remaining half of the tablets were permitted to cure at room temperature for approximately one day.

The tablets produced by both methods of curing resulted in a high quality rapidly dispersible units which had excellent mouthfeel and good taste. These products are deemed to be commercially valuable since it is known that the taste of acetaminophen is quite astringent and unpleasant to the consumer.

Thus, while there had been described what are presently believed to be the preferred embodiments of the present invention, other and further modification and changes can be made thereto without departing from the true spirit of the invention. It is intended to include all further and other modifications and changes which come within the true scope of the invention as set forth in the claims.

What is claimed is:

1. A cured comestible unit which can dissolve in the mouth in less than 10 seconds prepared by the method comprising:

mixing a chopped uncured shearform matrix and an additive;

compressing to a density of about 1.2 or less; and curing said compressed shearform matrix by subjecting it to conditions of heat, moisture and pressure which induce crystallization.

2. The unit of claim 1, wherein said shearform matrix further comprises a crystallization modifier.

3. The unit of claim 1, wherein said shearform matrix further comprises a binding agent.

4. The unit of claim 1, wherein said compressing comprises introducing the mix resulting from the mixing step to a unit dosage well and tamping said mix therein.

5. The unit of claim 1 wherein curing takes place in the presence of at least one additive selected from the group consisting of active ingredients, fragrances, dyes, sweeteners, crystallization modifiers, binders, lubricants, disintearants, alidants, and color additives.

6. The unit of claim 5, wherein said heat is increased under substantially constant moisture conditions.

7. The unit of claim 6, wherein said heat is increased by subjecting to microwave energy.

8. The unit of claim 1, wherein said additive comprises an active ingredient.

9. The unit of claim 8, wherein said active ingredient is selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

10. The unit of claim 8, wherein said active ingredient comprises an antacid and a pharmaceutical ingredient which is adversely affected by an acid environment.

11. The unit of claim 4, wherein said tamping is performed at a pressure of less than about 500 psi.

12. The unit of claim 11, wherein said pressure is less than about 250 psi.

13. The unit of claim 12, wherein said pressure is from about 20 to about 100 psi.

14. The unit of claim 1, which further comprises an effervescent disintegration agent.

* * * * *